(12) United States Patent
Grossoehmichen et al.

(10) Patent No.: US 11,235,150 B2
(45) Date of Patent: Feb. 1, 2022

(54) COCHLEAR IMPLANT LEADS AND METHODS OF MAKING THE SAME

(71) Applicant: ADVANCED BIONICS AG, Staefa (CH)

(72) Inventors: Martin Grossoehmichen, Nienhagen (DE); Konstantin Silberzahn, Zürich (CH); Tim Nauwelaers, Hannover (DE); Volkmar Hamacher, Hannover (DE)

(73) Assignee: Advanced Bionics AG, Staefa (CH)

( * ) Notice: Subject to any disclaimer, the term of this patent is extended or adjusted under 35 U.S.C. 154(b) by 248 days.

(21) Appl. No.: 16/294,790

(22) Filed: Mar. 6, 2019

(65) Prior Publication Data

US 2020/0188668 A1    Jun. 18, 2020

Related U.S. Application Data

(60) Provisional application No. 62/780,778, filed on Dec. 17, 2018.

(51) Int. Cl.
| | |
|---|---|
| *A61N 1/36* | (2006.01) |
| *A61B 1/227* | (2006.01) |
| *A61B 1/00* | (2006.01) |
| *A61N 1/05* | (2006.01) |
| *A61B 1/07* | (2006.01) |
| *A61N 1/375* | (2006.01) |

(52) U.S. Cl.
CPC ...... *A61N 1/36039* (2017.08); *A61B 1/00126* (2013.01); *A61B 1/07* (2013.01); *A61B 1/227* (2013.01); *A61N 1/0541* (2013.01); *A61N 1/36038* (2017.08); *A61N 1/375* (2013.01); *A61B 1/00167* (2013.01)

(58) Field of Classification Search
CPC ............ A61N 1/36039; A61N 1/36038; A61N 1/0541; A61N 1/375; A61B 1/00126; A61B 1/07; A61B 1/227; A61B 1/00167
See application file for complete search history.

(56) References Cited

U.S. PATENT DOCUMENTS

| | | | |
|---|---|---|---|
| 2006/0235500 A1 * | 10/2006 | Gibson | ................ A61N 1/0541 607/137 |
| 2013/0333918 A1 | 12/2013 | Lotfi et al. | |
| 2015/0305603 A1 * | 10/2015 | Gal | .................... A61B 1/00009 600/103 |
| 2015/0320550 A1 | 11/2015 | Downing et al. | |
| 2019/0111260 A1 | 4/2019 | Psaltis et al. | |
| 2019/0117258 A1 * | 4/2019 | Yamauchi | ................. A61F 2/18 |

FOREIGN PATENT DOCUMENTS

| | | |
|---|---|---|
| WO | WO 2014/105059 A1 | 7/2014 |
| WO | WO 2017/060832 A2 | 4/2017 |

* cited by examiner

*Primary Examiner* — Catherine M Voorhees
*Assistant Examiner* — Roland Dinga
(74) *Attorney, Agent, or Firm* — Henricks Slavin LLP

(57) ABSTRACT

A cochlear implant, for use with a micro camera, including a stimulation assembly, a cochlear lead with an electrode array, a lens associated with the distal region of the electrode array, an optical fiber bundle that extends proximally from the lens and outwardly from the proximal region of the cochlear lead, a camera interface in which the proximal end of the optical fiber bundle is located and that is configured to receive the micro camera, and at least one illumination guide that extends from the camera interface to the cochlear lead.

19 Claims, 8 Drawing Sheets

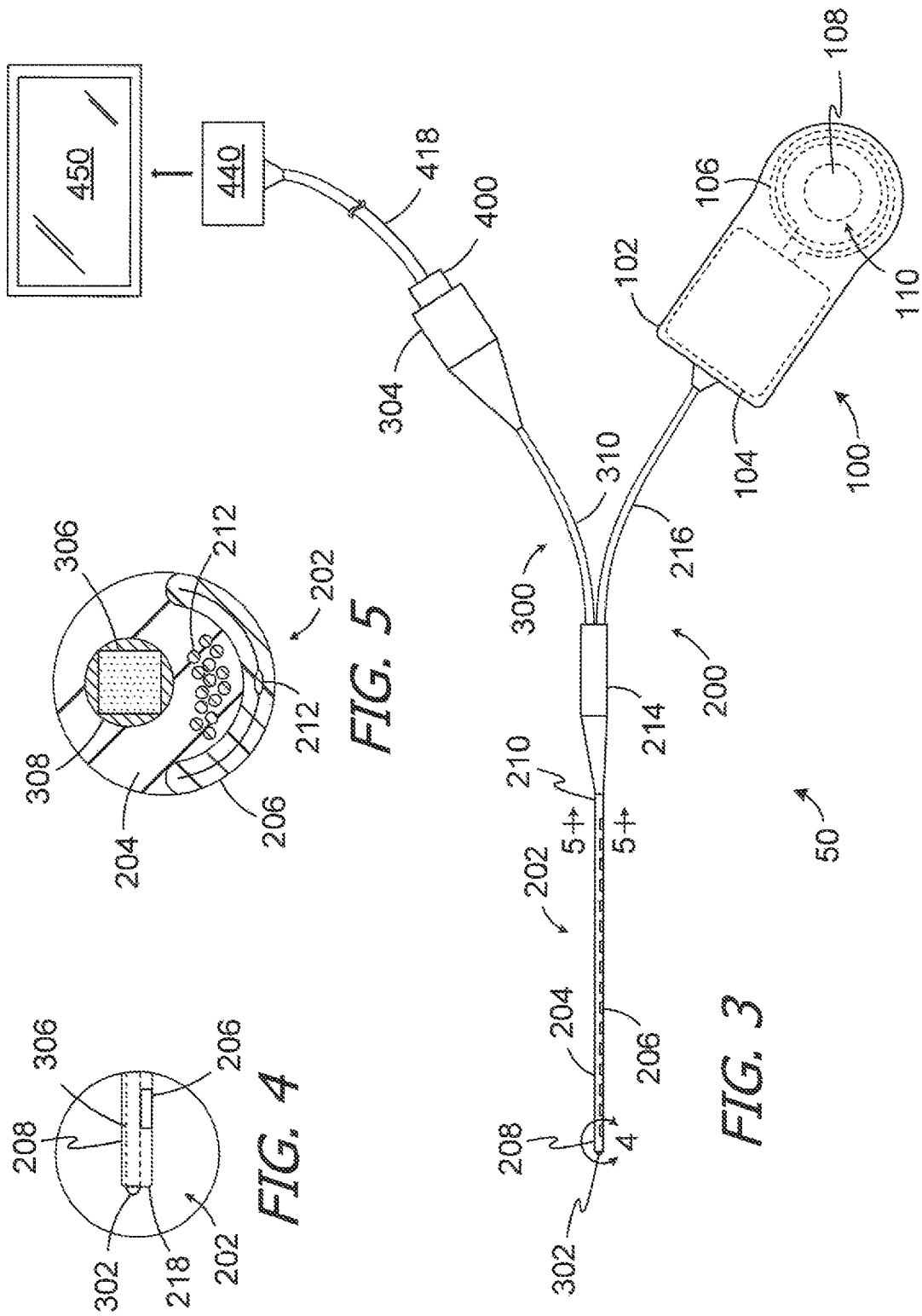

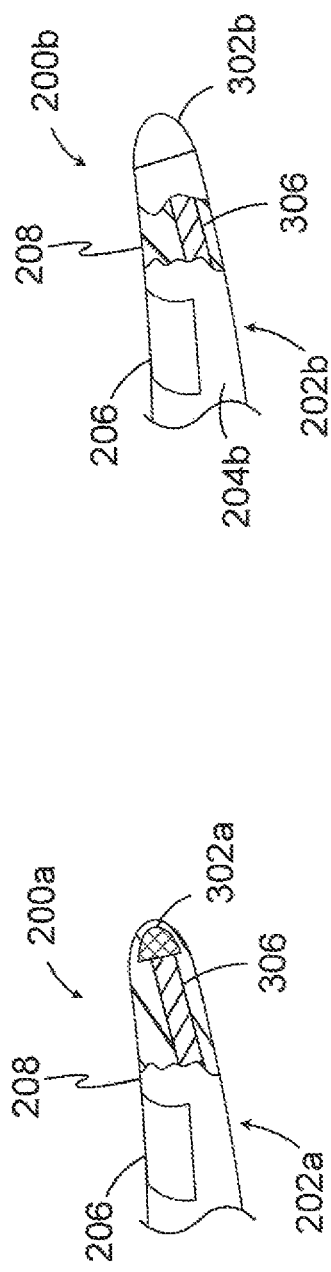
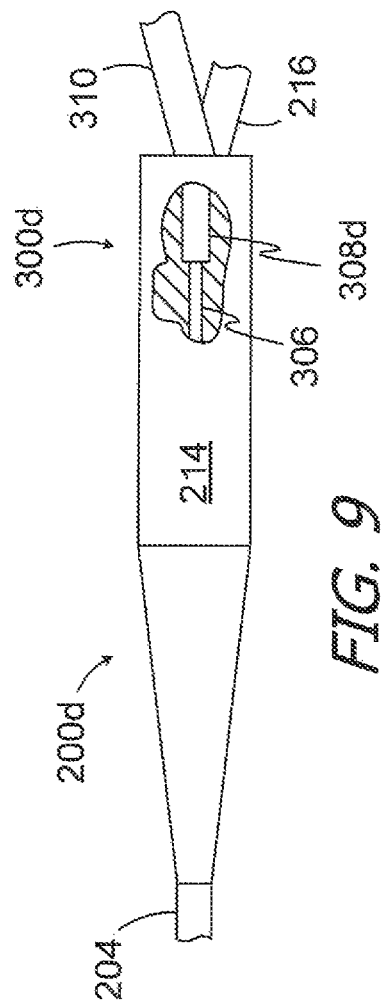
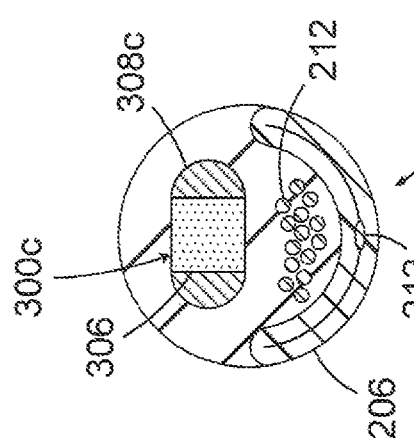

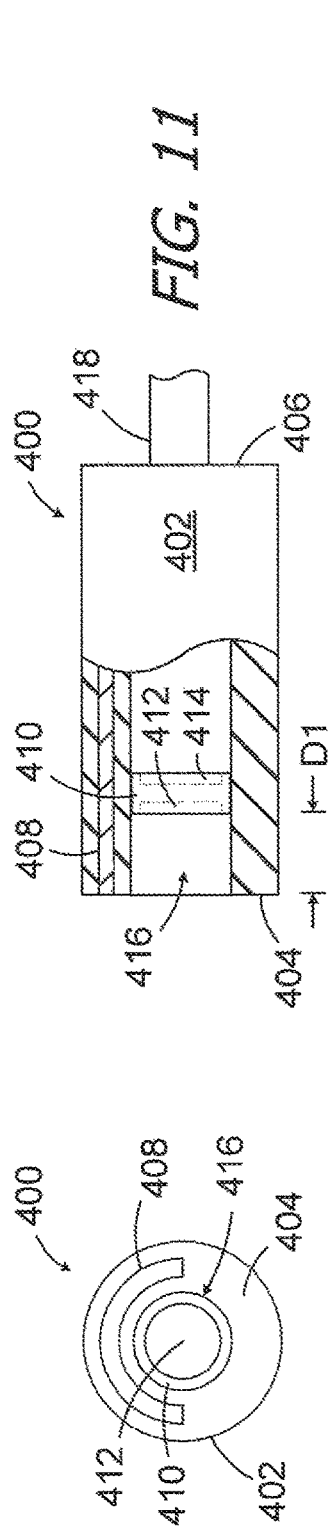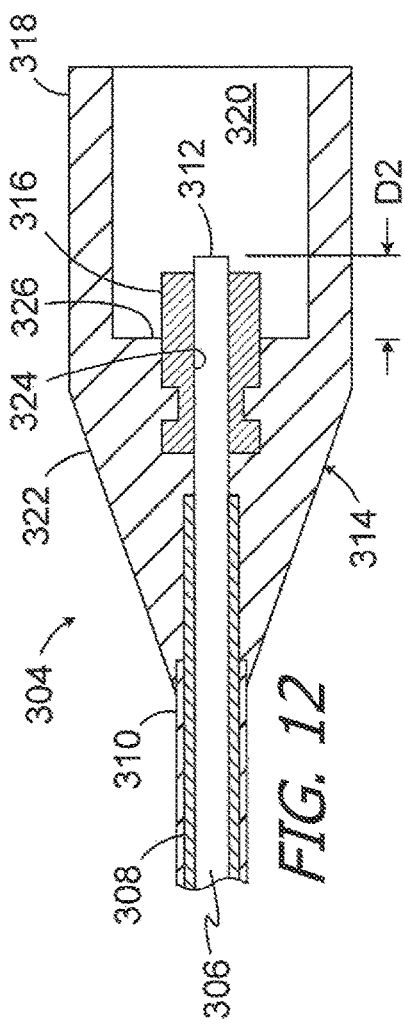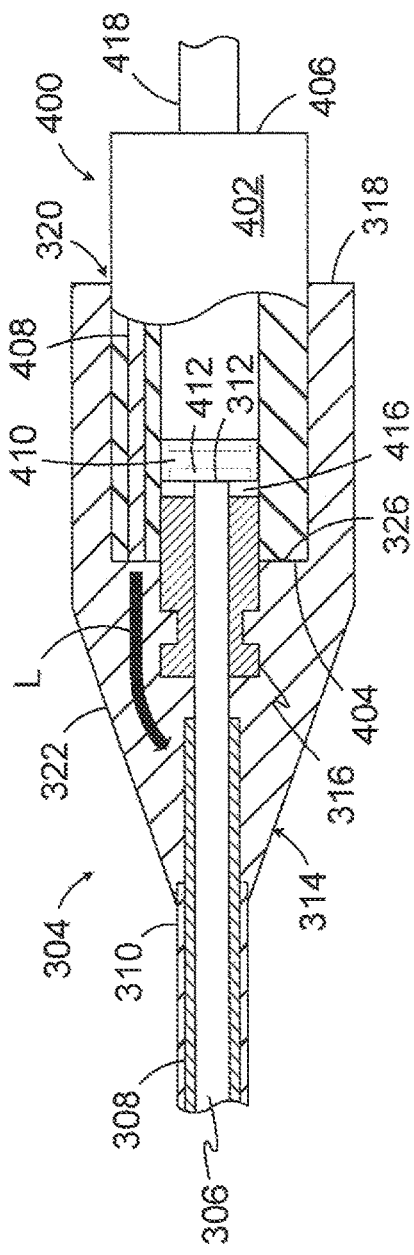

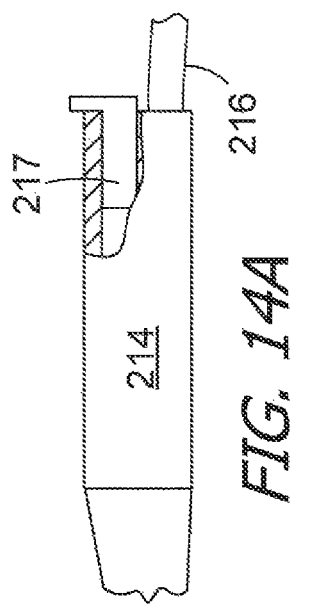
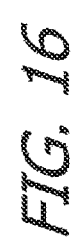
FIG. 14A
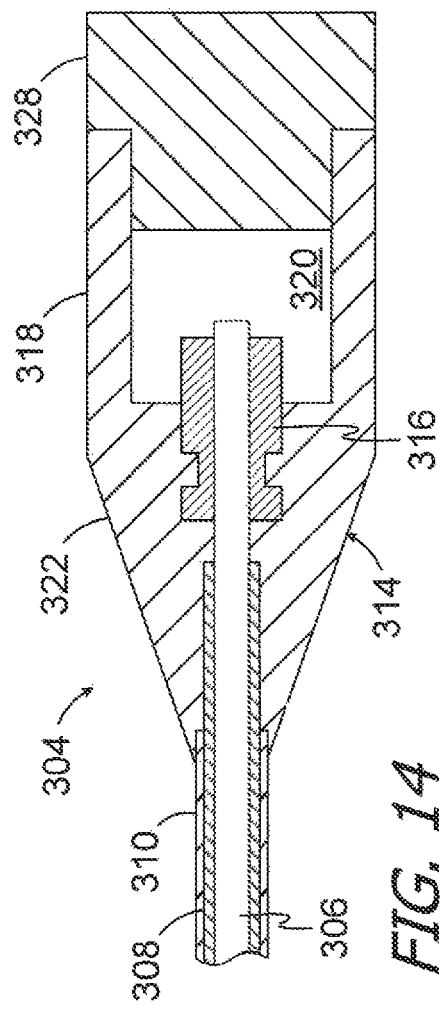
FIG. 14
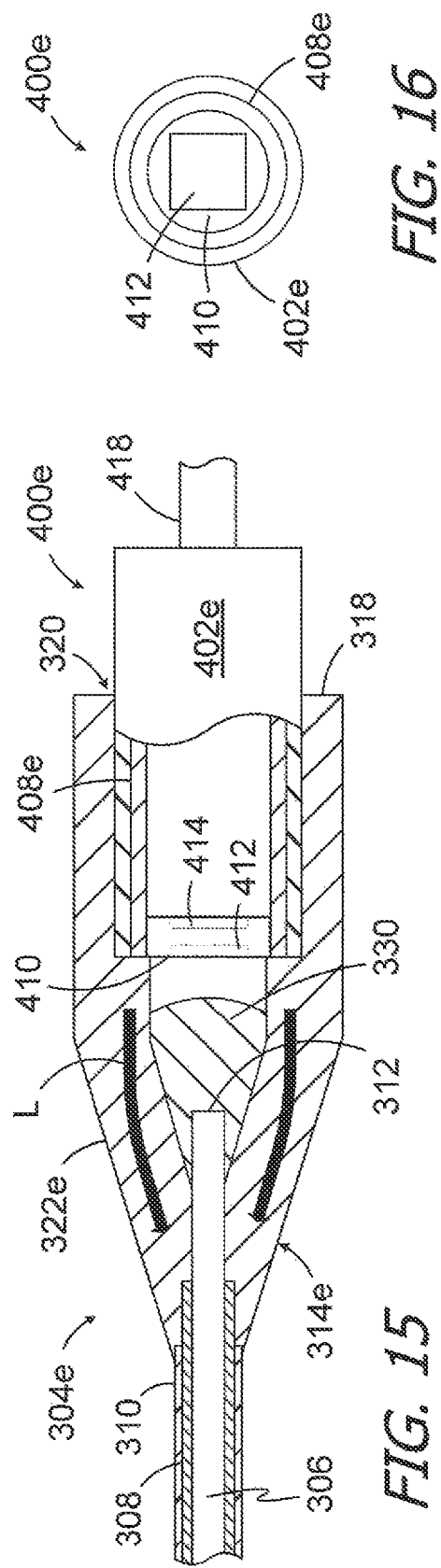
FIG. 16
FIG. 15

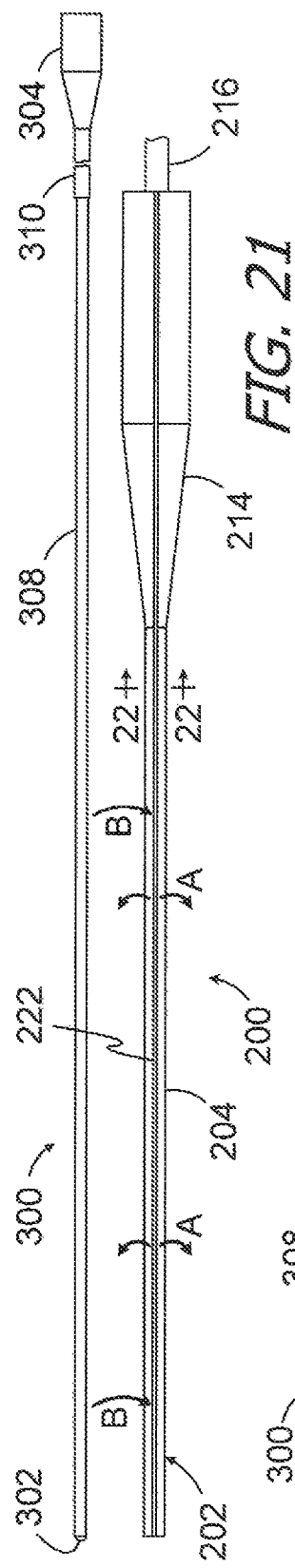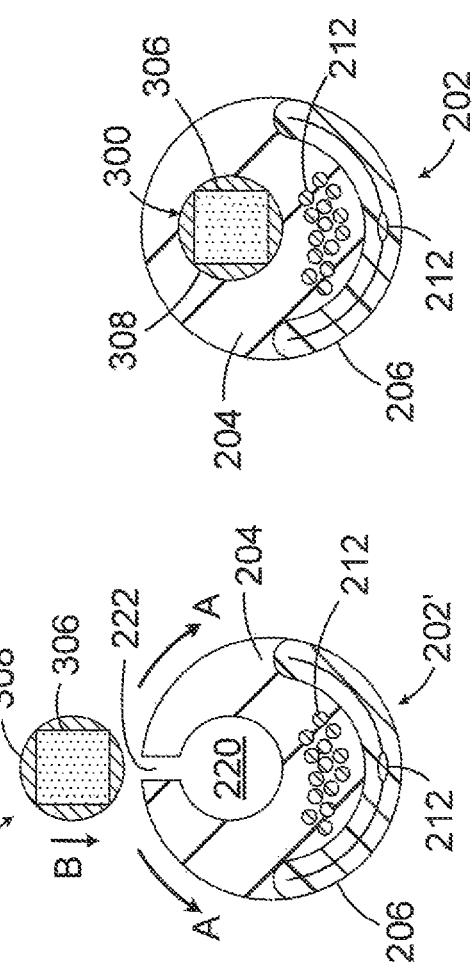

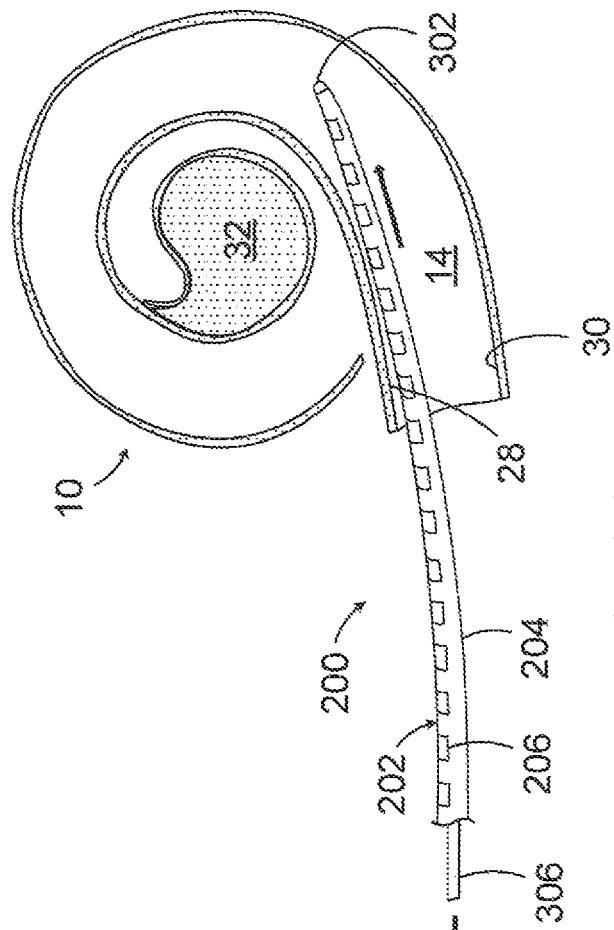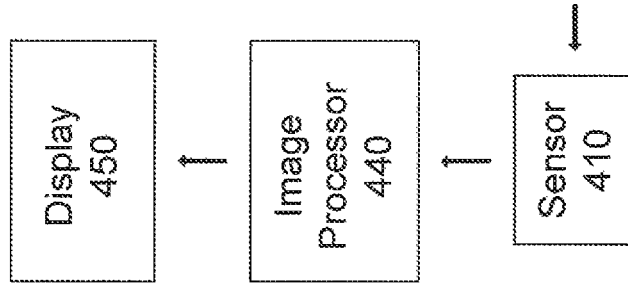
FIG. 26

COCHLEAR IMPLANT LEADS AND METHODS OF MAKING THE SAME

CROSS-REFERENCE TO RELATED APPLICATIONS

This application claims the benefit of U.S. Provisional Application No. 62/780,778, filed Dec. 17, 2018, which is incorporated herein by reference.

BACKGROUND

1. Field

The present disclosure relates generally to the implantable portion of implantable cochlear stimulation (or "ICS") systems.

2. Description of the Related Art

Referring to FIGS. 1 and 2, the cochlea 10 is a hollow, helically coiled, tubular bone (similar to a nautilus shell) that is divided into the scala vestibuli 12, the scala tympani 14 and the scala media 16 by the Reissner's membrane 18 and the basilar membrane 20. The cochlea 10, which typically includes approximately two and a half helical turns, is filled with a fluid that moves in response to the vibrations coming from the middle ear. As the fluid moves, a tectorial membrane 22 and thousands of hair cells 24 are set in motion. The hair cells 24 convert that motion to electrical signals that are communicated via neurotransmitters to the auditory nerve 26, and transformed into electrical impulses known as action potentials, which are propagated to structures in the brainstem for further processing. Many profoundly deaf people have sensorineural hearing loss that can arise from the absence or the destruction of the hair cells 24 in the cochlea 10.

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant") having an implant lead with an electrode array, a sound processor unit (e.g., a body worn processor or behind-the-ear processor) that communicates with the cochlear implant, and a microphone that is part of, or is in communication with, the sound processor unit. The cochlear implant electrode array includes a flexible body formed from a resilient material such as liquid silicone rubber ("LSR") and a plurality of electrically conductive contacts (e.g., sixteen platinum contacts) spaced along a surface of the flexible body. The contacts of the array are connected to platinum lead wires that extend through the flexible body. The electrode array is surgically inserted into the cochlea and, once implanted, the contacts face the modiolus within the cochlea.

The present inventors have determined that conventional electrode leads are susceptible to improvement. For example, the electrode array is typically inserted the hollow, helically coiled cochlea without any visual feedback. Absent visual feedback, the surgeon must rely on the tactile feedback that occurs when the electrode array is obstructed as it is moving in the apical direction. Such obstruction can, however, result in misplacement of and damage to the electrode array as well as unwanted trauma to the cochlea. For example, misplacement of the electrode array reduces the effectiveness of the cochlear implant and may necessitate a revision surgery to more accurately place the electrode array. Misplacement of the electrode array as it is moving in the apical direction can resulting in scraping of the cochlea, folding of the electrode array, buckling of the electrode array, and breaching the basilar membrane. The associated damage to the inner ear can result in a reduction in (or loss of) the residual hearing that was present prior to the cochlear implant insertion, thereby reducing the likelihood that the cochlear implant recipient will be able to benefit from combined electro-acoustic hearing assistance.

One proposed method of improving placement of electrode arrays despite the lack of visual feedback involves the use of optical sensors on the electrode array. For example, WO2017060832 discloses cochlear leads with optical waveguides and light-based sensors that may be used to determine the proximity of the associated portion of the electrode array cochlea or to estimate the three-dimensional shape of the cochlea. Although the cochlear leads disclosed in WO2017060832 represent an advance in the art, the present inventors have determined that they are susceptible to improvement. For example, the present inventors have determined that it would be desirable to provide the surgeon with visual feedback of the cochlea (as opposed to an estimated representation), and that the optical waveguide configuration disclosed in WO2017060832 may not provide suitable resolution. The present inventors have further determined that it would be desirable to facilitate the incorporation of a conventional optical sensor/camera into visual feedback apparatus that is part of a cochlear implant electrode array.

SUMMARY

A cochlear implant in accordance with one of the present inventions may include a stimulation assembly, a cochlear lead with an electrode array, a lens associated with the distal region of the electrode array, an optical fiber bundle that extends proximally from the lens and outwardly from the proximal region of the cochlear lead, a camera interface in which the proximal end of the optical fiber bundle is located and that is configured to receive a micro camera, and at least one illumination guide that extends from the camera interface to the cochlear lead. Systems in accordance with the present inventions may include a micro camera and such a cochlear implant. There are a number of advantages associated with such cochlear implants and systems. For example, use of the optical fiber bundle results in superior images and the camera interface may be configured in such a manner that conventional (or "off the shelf") micro cameras may be connected thereto.

A method in accordance with the present inventions includes the step of inserting a portion of an endoscope into a lumen located within a cochlear lead electrode array that includes a flexible body and a plurality of electrically conductive contacts on the flexible body. There are a number of advantages associated with such a method. For example, the endoscope can provide visual feedback of the cochlea during an implantation procedure.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 3 is a view of an implantable cochlear stimulator, a micro camera and a monitor in accordance with one embodiment of a present invention.

FIG. 4 is an enlarged view of a portion of FIG. 3.

FIG. 5 is a section view taken along line 5-5 in FIG. 3.

FIG. 6 is a side, cutaway view of the tip portion of a cochlear lead in accordance with one embodiment of a present invention.

FIG. 7 is a side, cutaway view of the tip portion of a cochlear lead in accordance with one embodiment of a present invention.

FIG. 8 is a section view of a cochlear lead in accordance with one embodiment of a present invention.

FIG. 9 is a top, cutaway view of the handle portion of a cochlear lead in accordance with one embodiment of a present invention.

FIG. 10 is an end view of an exemplary micro camera.

FIG. 11 is a side, cutaway view of the exemplary micro camera illustrated in FIG. 10.

FIG. 12 is a section view of the camera interface of the implantable cochlear stimulator illustrated in FIG. 3.

FIG. 13 is a section view of the camera interface of the implantable cochlear stimulator illustrated in FIG. 3 with the micro camera illustrated in FIGS. 10 and 11 mounted thereto.

FIG. 14 is a section view of the camera interface of the implantable cochlear stimulator illustrated in FIG. 3 with a cap connected thereto.

FIG. 14A is a side, cutaway view of a portion of a cochlear lead in accordance with one embodiment of a present invention.

FIG. 15 is a section view of a camera interface in accordance with one embodiment of a present invention with a micro camera mounted thereto.

FIG. 16 is an end view of the micro camera illustrated in FIG. 15.

FIG. 21 is a plan view of a portion of a cochlear lead manufacturing process in accordance with one embodiment of a present invention.

FIG. 22 is a section view taken along line 22-22 in FIG. 21.

FIG. 23 is a section view of a portion of a cochlear lead manufacturing process in accordance with one embodiment of a present invention.

FIG. 24 is a plan view of a portion of a cochlear lead manufacturing process in accordance with one embodiment of a present invention.

FIG. 25 is a section view taken along line 25-25 in FIG. 24.

FIG. 26 is a section view showing a cochlear lead in accordance with the present inventions being implanted into a cochlea.

DETAILED DESCRIPTION OF THE EXEMPLARY EMBODIMENTS

Figure 2:
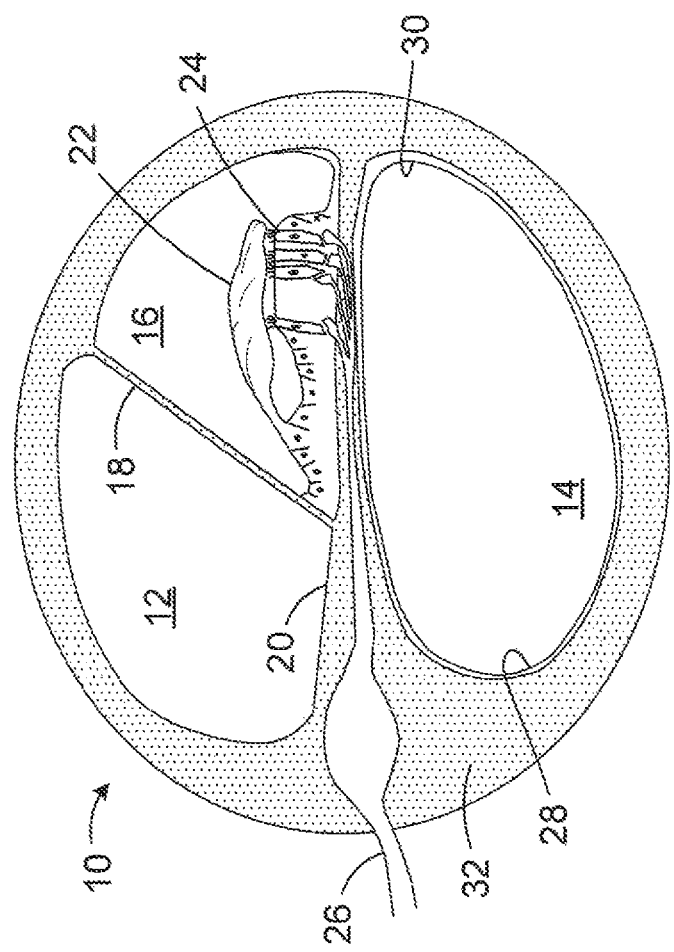
FIG. 2 is another section view of the cochlea.

The following is a detailed description of the best presently known modes of carrying out the inventions. This description is not to be taken in a limiting sense, but is made merely for the purpose of illustrating the general principles of the inventions.

One example of a cochlear implant (or "implantable cochlear stimulator") in accordance with at least some of the present inventions is generally represented by reference numeral 50 in FIG. 3. Referring also to FIGS. 4 and 5, the cochlear implant 50 includes a stimulation assembly 100, a cochlear lead 200 that is operably connected to the stimulation assembly, and an endoscope 300 that is associated with the cochlear lead. The endoscope 300 may, for example, be connected to a conventional micro camera 400. Images from the micro camera 400 may be processed by an image processor 440, which is in turn connected to a display 450 that may be observed by the surgeon performing implantation surgery.

Figure 1:
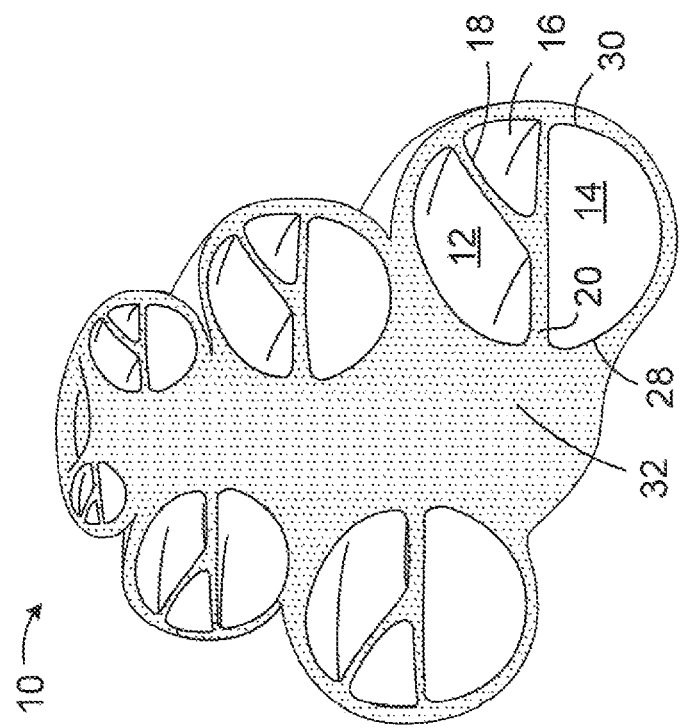
FIG. 1 is a section view of a cochlea.

The exemplary stimulation assembly 100 may include a flexible housing 102 formed from a silicone elastomer or other suitable material, a processor assembly 104 with a stimulation processor, an antenna 106 that may be used to receive data and power by way of an external antenna that is associated with, for example, a sound processor unit. A positioning magnet 108 (FIG. 1) is located within a magnet pocket 110. The magnet 108 is used to maintain the position of a headpiece transmitter over the antenna 106. The stimulation assembly 100 may, in some instances, be configured is manner that facilitates magnet removal and replacement. Here, the housing 102 may be provided with a magnet aperture (not shown) that extends from the magnet pocket 110 to the exterior of the housing.

The exemplary cochlear lead 200 may include an electrode array 202 with a flexible body 204 and a plurality of electrically conductive contacts 206 (e.g., the sixteen contacts 206) spaced along the flexible body. The electrode array 202 may be a pre-curved array that has a tip (or "distal region") 208, a base (or "proximal region") 210 and, when in an unstressed (or "relaxed") state, an overall preset spiral shape that corresponds to that of the cochlea. Other electrode arrays, such as those that are only slightly pre-curved or those that have no pre-curvature, may also be employed. In the illustrated implementation, the flexible body 204 has a circular shape in cross-section. The cross-sectional shape may, in other implementations, be non-circular or a truncated circular shape with a flat surface. Suitable materials for the flexible body 204 include, but are not limited to, LSR, translucent or transparent flexible materials such as polydimethylsiloxane ("PDMS") (e.g., NuSil MED-4860 and MED-6215), high temperature vulcanization ("HTV") silicone rubbers, room temperature vulcanization ("RTV") silicone rubbers, and thermoplastic elastomers ("TPEs"). The exemplary contacts 206 are semi-circular and are located on the side of the flexible body that will face the modiolus (and medial wall). Such a contact may be formed by, for example, positioning the lead wire 212 that will be connected to the contact within a tubular workpiece, and then applying heat and pressure to the workpiece to form a semi-circular contact that is connected to a lead wire, as is discussed below with reference to FIG. 17. In other implementations, the contacts may be tubular structures that extend completely around the flexible body, i.e., extend 360 degrees around the flexible body. Suitable materials for the contacts 206 include, but are not limited to, platinum, platinum-iridium, gold and palladium. The contacts 206 may be referred to in numbered order, 1st through 16th, with the contact closest to the tip 208 being the 1st contact and the contact closest to the proximal region 210 being the 16th contact.

In addition to the electrode array 202, the exemplary cochlear lead 200 includes an array handle 214 mounted onto the proximal region 210, with a rectangular portion and a tapered portion, which may be gripped by the surgeon during the implantation surgery. The handle 214 also provides tension relief for the lead wires 212, which do not run straight through the handle. A tubular member 216, which may consist of tubes of different sizes, extends from the handle 214 to the housing 102. The lead wires 212 extend through the flexible body 204 and tubular member 216 to a connector (not shown) in the housing 102.

During use, a sound processor (not shown), such as a BTE sound processor or body-worn sound processor, converts electrical signals from a microphone into stimulation data. The stimulation data and, in many instances power, is supplied to the stimulation assembly 100. For example, stimulation data and power from the sound processor may be transcutaneously transmitted to the stimulation assembly antenna 106 by a headpiece with an antenna. The stimulation processor in the processor assembly 104 converts the stimulation data into stimulation signals that stimulate the contacts 206 of the electrode array 202.

The exemplary endoscope 300 illustrated in FIGS. 3-5 may include a lens 302, a camera interface 304, an optical fiber (or "wave guide") bundle 306 that extends from the lens, through the electrode array 202 and to the camera interface, and one or more illumination guides 308 that extends from the camera interface to the cochlear lead 200. The camera interface 304 may be used to connect a conventional very small camera (or "micro camera") to the endoscope 300 in such a manner that the proximal end of the optical fiber bundle 306 is positioned adjacent to the micro camera's sensor and light from the micro camera's illumination source can be transmitted to the illumination guides 308.

Referring more specifically to FIG. 4, the exemplary lens 302 is located at, and projects outwardly from, the distal end 218 of the electrode array 202. In the illustrated implementation, the lens 302 and the electrode array 202 are separate structural elements, and the lens is secured to the distal end of the optical fiber bundle 306 prior to the optical fiber bundle be inserted into the electrode array in the manner described below with reference to FIGS. 21-23. In other exemplary configurations, a lens may be embedded into the distal region of an electrode array. For example, the exemplary cochlear lead 200a illustrated in FIG. 6 (which may be otherwise identical to cochlear lead 200) includes an electrode array 202a with a lens 302a embedded into the distal region 208a. The distal end of the optical fiber bundle 306 may be positioned adjacent to (or in contact with) the lens 302a during the assembly process. The lenses 302 and 302a may be formed from glass or any other suitable material. In other implementations, the lens may be an integral part of the cochlear lead. For example, at least the distal tip of the flexible body 204b in the exemplary cochlear lead 200b illustrated in FIG. 7 is formed from transparent material (e.g., PDMS NuSil MED-6215) that is molded into a lens 302b with the appropriate curvature, surface quality and refractive index. Here, the portion of the mold that is used to form the flexible body 204b may include a polished glass insert in the region that defines the lens 302b.

Turning back to FIGS. 3-5, the optical fiber bundle 306 and illumination guides 308 of the exemplary endoscope 300 extend from the camera interface 304, through a tube 310 or other protective exterior layer (e.g., a protective layer formed by dip coating or an over molding process), and into the cochlear lead 200 at the proximal end of the handle 214. The optical fiber bundle 306 carries light that is focused onto the fibers by the lens 302 (or other lens) to the micro camera 400 (discussed below) that is mounted to the camera interface 304, while the illumination guides 308 transmit light from a light source associated with the camera interface (e.g., a light source on the micro camera 400, as shown, or a separate light source) to the cochlear lead 200 to illuminate the cochlea, at least in area adjacent to the distal region 208. The optical fiber bundle 306 extends from the camera interface 304 to the associated lens (e.g., lens 302) while, depending on the light transmission properties of the flexible body 204 and handle 214, the illumination guides 308 may extend from the camera interface 304 only into the handle, or only into the proximal region 210 of the electrode array 202, or only into the distal region 208, or to any location between the proximal and distal region. Suitable materials for the optical fibers include flexible image fibers, flexible glass fibers, and flexible plastic fibers that can accommodate the bend radii associated with the cochlea. The optical fiber bundle 306 may include one or more fibers. The number of fibers in the optical fiber bundle 306 will depend on the intended application, the cross-sectional area of the fibers, and the available space within the electrode array 202 and remainder of the cochlear lead 200. In at least some implementations, the diameter of the optical fibers may range from 1 μm to 50 μm. In some implementations, laser written waveguides such as those disclosed in WO2017/060832 may be employed, although the image quality may be lower than that associated with an optical fiber bundle. The exemplary illumination guides 308, which run parallel to the optical fiber bundle 306, may be formed from molded or cast PDMS or from other suitable flexible light transmissive materials. In some instances, there may be a coating (not shown) between the optical fiber bundle 306 and the illumination guides 308 that optically isolates optical fiber bundle from the illumination guides.

It should be noted here that although there are four (4) partial-circle shaped illumination guides 308 in the exemplary endoscope 300 that extend to the distal region 208, the number, shape, length and size of the illumination guides configurations may vary, as was alluded to above. By way of example, but not limitation, the endoscope 300c illustrated in FIG. 8 (which is otherwise identical to endoscope 300) includes a pair of the semi-circular illumination guides 308c that extend only to the 16$^{th}$ electrode in the proximal region 210. Turning to FIG. 9, the exemplary endoscope 300d (which is otherwise identical to endoscope 300) includes illumination guides 308 that only extend into the handle 214, which may be formed from PDMS or other transparent material, as may the flexible body 204 in such instances.

As noted above, the camera interface 304 may be configured to connect a conventional micro camera to the endoscope 300 (or endoscopes 300c-300d) in such a manner that the proximal end 312 of the optical fiber bundle 306 is positioned adjacent to the camera's sensor and light from the camera's illumination source can be transmitted to the illumination guides 308. One example of a micro camera, which is generally represented by reference numeral 400 in FIGS. 10 and 11, includes a housing 402 with front and rear ends 404 and 406, a light source 408, and a light sensor 410. The exemplary housing 402 may be cylindrical in shape (as shown) or any other suitable shape. The exemplary light source 408 may be, for example, an LED and may be semicircular (as shown) or other suitable shapes. Although the exemplary light sensor 410 includes a CCD 412 and associated circuitry 414, other suitable light sensing devices (e.g., a CMOS) may be employed. An aperture 416 that is aligned with the light sensor 410 extends inwardly from the front end 404 of the housing 202. A cable 418 that extends from the rear end 406 of the housing may be used to connect the micro camera 400 to the image processor 440, which is in turn connected to the display 450 or other viewing device.

Commercially available micro cameras that may be connected to the endoscope 300 in its present form, or in slightly different forms to accommodate particular cameras, include but are not limited to, the FISBA FISCam™ micro camera with the front lens removed.

As illustrated in FIGS. 12 and 13, the exemplary camera interface 304 includes a housing 314 and a connector 316. The exemplary housing 314 has a camera portion 318, which defines a camera receptacle 320, and a light guide portion 322, through which the optical fiber bundle 306 and the illumination guides 308 extend. The connector 316 (here, a plug) is configured to mate with the camera housing aperture 416, which defines a receptacle for the connector 316, and includes a lumen 324 through which the optical fiber bundle 306 extends. The optical fiber bundle 306 is secured to the connector 316 and the position of the optical fiber bundle proximal end 312 within the housing camera receptacle 320 and relative to the connector 316 is fixed. The respective configurations of the camera interface 304 and the micro camera 400 result in the proximal end 312 of the optical fiber bundle 306 being in contact with the CCD 412 or in close proximity to the CCD (i.e., no more than 0.1 mm from the CCD). In the case the exemplary embodiment illustrated in FIGS. 10-13, the depth D1 (FIG. 11) of the aperture 416 is equal to, or differs by no more than 0.01 mm from, the distance D2 (FIG. 12) that the optical fiber bundle proximal end 312 extends beyond the distal end 326 of the camera receptacle 320. As a result, when the micro camera 400 is fully inserted into the camera interface 304, and the housing front end 404 touches the distal end 326 of the camera receptacle 320, the optical fiber bundle proximal end 312 will be in contact with, or in close proximity to, the CCD 412.

With respect to manufacturing and materials, the camera interface housing 314 may be formed from a resilient transparent material, such as transparent PDMS, with the connector 316 and proximal portion of optical fiber bundle 306 and illumination guides 308 in the mold. During use, the transparent housing allows light L (FIG. 13) from the light source 408 can travel through the transparent housing 314 to the illumination guides 308.

The dimensions (e.g., the inner diameter) of the camera receptacle 320 may be slightly less than the outer dimension (e.g., outer diameter) of the resilient camera housing 402 to provide a tight fit. For example, the inner diameter of the camera receptacle 320 may be 0.01 to 0.02 mm less than the outer diameter of the camera housing 402. The connector 316 may be formed from a relatively rigid material such as PEEK, while the camera housing 402 may be formed from relatively rigid materials such as stainless steel. The dimensions should also result in a tight fit which, in combination with the use of rigid material, facilitates precise positioning of the optical fiber bundle proximal end 312 relative to the CCD 412 and stabilizes the CCD relative to the optical fiber bundle proximal end.

The camera 400 may be removed from the endoscope 300 at the end of the implantation procedure. To that end, and turning to FIG. 14, the exemplary camera interface 304 may be provided with a cap 328 that may be used to cover the camera receptacle 320. Covering the camera receptacle 320 will, among other things, prevent the formation of fibrosis within the camera receptacle. The optical fiber bundle 306 and the illumination guides 308 may also be removed from the cochlear lead 300 in some instances, especially those in which the lens is part of the cochlear lead (e.g., lenses 302a and 302b in FIGS. 6 and 7). Here, a plug 217 may be inserted into the proximal end of the lumen (discussed below) through which the optical fiber bundle 306 and the illumination guides 308 pass, as shown in FIG. 14A. The camera interface 304 may also simply be severed from the remainder of the endoscope 300.

The micro cameras and camera interfaces are not limited to the exemplary embodiments discussed above. By way of example, but not limitation, the exemplary micro camera 400e illustrated in FIGS. 15 and 16, which does not include a connector similar to connector 416, includes a housing 402e and an annular light source 408e that encircles the light sensor 410. The associated camera interface 304e includes a housing 314 with a camera portion 318, which defines a camera receptacle 320, and a light guide portion 322e, through which the optical fiber bundle 306 and the illumination guides 308 extend. There is no connector similar to connector 316. The exemplary camera interface 304e also includes a lens 330 with a convex surface curvature that focuses light from the optical fiber bundle 306 onto a predetermined location within the housing 314e and, in particular, onto the CCD 412 of the light sensor 410. The lens may be formed from the same material as the housing 402 (e.g., PDMS) or other suitable lens materials. Here too, the dimensional relationships between the camera housing 402e and interface housing camera portion 318 result in a tight fit that holds the micro camera 400e in place.

Figure 17:
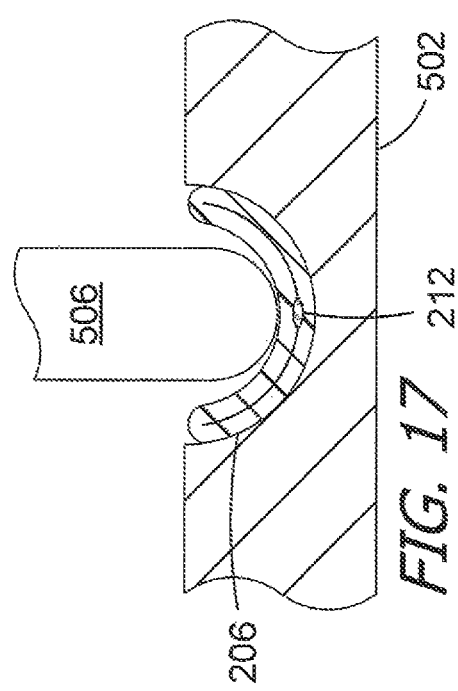
FIG. 17 is a section view of a portion of a cochlear lead manufacturing process in accordance with one embodiment of a present invention.
Figure 18:
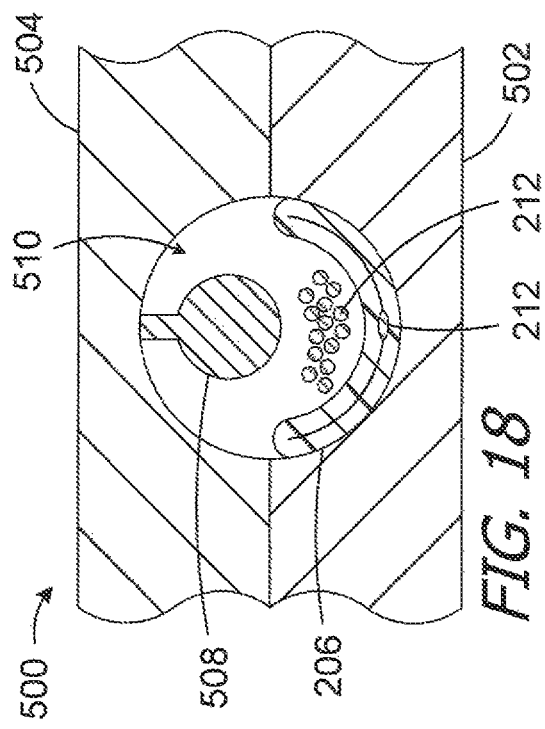
FIG. 18 is a section view of a portion of a cochlear lead manufacturing process in accordance with one embodiment of a present invention.
Figure 19:
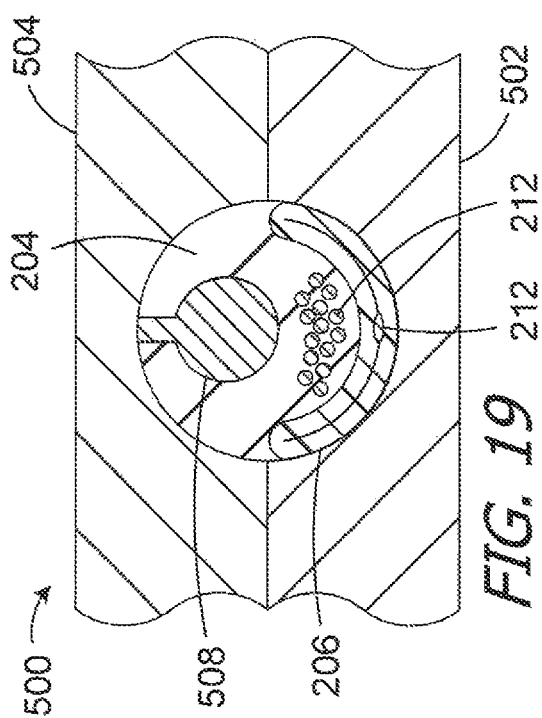
FIG. 19 is a section view of a portion of a cochlear lead manufacturing process in accordance with one embodiment of a present invention.
Figure 20:
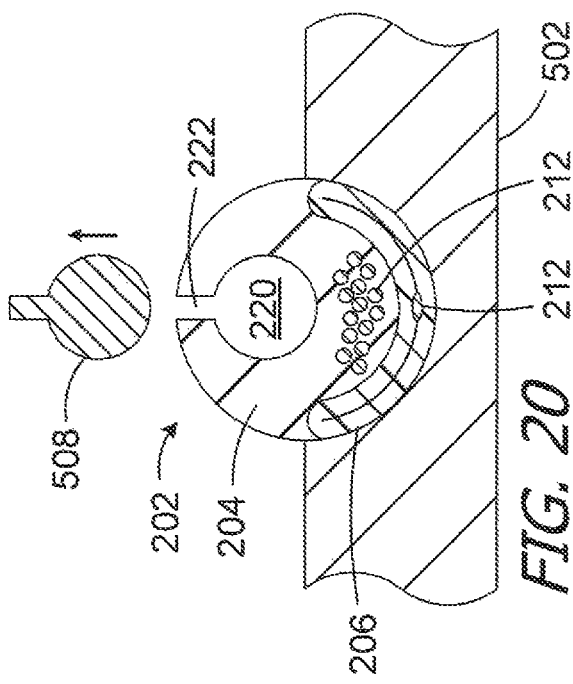
FIG. 20 is a section view of a portion of a cochlear lead manufacturing process in accordance with one embodiment of a present invention.

The endoscope 300 may be incorporated into the cochlear lead 200, either temporarily or permanently, in a variety of ways. In some exemplary manufacturing methods, a lumen may be formed within the cochlear lead 200 and various portions of the endoscope 300 may thereafter be inserted into the lumen. One exemplary method involves forming a lumen that extends entire length of the cochlear lead 200 and a slit that provides access to the lumen. Referring to FIGS. 17-20, each of the electrically conductive contacts 206 of the cochlear lead 200 may be formed by sequentially placing tubular workpieces into spaced locations in the bottom portion 502 of a mold 500 (which also includes top portion 504), placing the end of a respective lead wire 212 into each tubular workpiece, and then applying heat and pressure to the workpiece (e.g., with a weld tip 506) to form a series of spaced a semi-circular contacts 206 that are each connected to a separate lead wire 212 (FIG. 17). A lumen and slit forming insert 508 may be positioned within the mold cavity 510 (FIG. 18). PDMS or other suitable resilient material may then be injected (or otherwise introduced) into the mold cavity 510 to form the flexible body 204 (FIG. 19). The insert 508 may be withdrawn from the flexible body 204 after the resilient material has cured, thereby exposing the lumen 220 and the slit 222 (FIG. 20), and completing the cochlear lead 200. The slit 222 extends from the outer surface of the flexible body 204 to the lumen 220. Additional details concerning cochlear lead molding processes may be found in, for example, WO2018/031025, which incorporated herein by reference in its entirety.

Next, the endoscope 300 (or other endoscope) may be inserted into the cochlear lead 200 by way of the slit 222. Referring to FIGS. 21 and 22, the slit 222 may be enlarged by pulling apart portions of the flexible body 204 (note arrows A) so that the endoscope 300 can be inserted through the slit and into the lumen 220 (note arrows B). The slit 222 may then be filed with PDMS, medical grade adhesive or other suitable material to complete the assembly, as shown in FIG. 23.

Other exemplary manufacturing methods involve forming the cochlear lead with a lumen and no slit. Turning to FIGS. 24 and 25, the exemplary cochlear lead 200b (also described above with reference to FIG. 7) includes a flexible body 204b with a distal tip that is molded into the lens 302b. A lumen 220 that extends from the proximal end of the handle 214 to the lens 302b may be formed by placing an insert into the mold and then pulling the insert longitudinally out of the lead. There is no slit. Accordingly, the optical fiber bundle 306 and illumination guides 308 are inserted into the proximal end of the lumen 220 (FIG. 24) and are pushed distally until the distal end of the optical fiber bundle 306 abuts the lens 302b in the manner illustrated in FIG. 7, thereby forming an endoscope.

As illustrated for example in FIG. 26, images from the lens 302 (or other lens described above) of the present endoscope are delivered to the micro camera light sensor 410 as pixels by way of the optical fiber bundle 306 during the implantation of the electrode array 202 into the cochlea 10. In some implementations, each pixel corresponds to the light delivered by a single optical fiber within the bundle. In others, depending upon the pixel size of the sensor and the cross-sectional size of a single optical fiber, one pixel may capture the light from several optical fibers or the light from one optical fiber may be captured by several pixels. The image processor 440 interpolates between and generates a complete, digitally stabilized image that may be displayed to the surgeon on the display 450. The display may be in the form of a monitor, the lenses of a surgical microscope or spectacles, or 3D goggles (using virtual or augmented reality). The image may also be used in combination with robotic insertion tools. The brightness of each pixel, or of a plurality of pixels, may be used by the image processor 440 to identify and highlight intracochlear structures (e.g. the basilar membrane, modiolus, etc.), and such identification may be improved through the use of infrared light or fluorescence imaging can be used. The distance between the tip of the electrode array 202 and intracochlear structures may also be estimated and displayed as well as used to detect impending collisions and provide an acoustic or visual warning to the surgeon. In addition, previously obtained patient-specific cochlear images and models may be overlaid onto the images obtained by way of the optical fiber bundle 306 to improve the insertion procedure.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant for use with a micro camera including a housing, a light source and a light sensor, the cochlear implant comprising:
   a stimulation assembly including a housing, an antenna within the housing, and a stimulation processor within the housing operably connected to the antenna;
   a cochlear lead, operably connected to the stimulation processor, defining a proximal region and a distal region and including an electrode array with a flexible body and a plurality of electrically conductive contacts on the flexible body;
   a lens associated with the distal region of the electrode array;
   an optical fiber bundle, including a distal end adjacent to the lens and a proximal end, that extends from the lens, through the flexible body, and outwardly from the proximal region of the electrode array;
   a camera interface, in which the proximal end of the optical fiber bundle is located, configured to receive the micro camera in such a manner that the proximal end of the optical fiber bundle is adjacent to the light sensor and including an interface connector, through which the optical fiber bundle passes, that is configured to mate with an aperture on the micro camera housing; and
   at least one illumination guide that extends from the camera interface to the cochlear lead.

2. A cochlear implant as claimed in claim 1, wherein the lens is secured to the optical fiber bundle and projects outwardly from the flexible body.

3. A cochlear implant as claimed in claim 1, wherein the lens is embedded within the flexible body.

4. A cochlear implant as claimed in claim 1, wherein the lens is a molded portion of the flexible body.

5. A cochlear implant as claimed in claim 1, wherein the at least one illumination guide extends to distal region of the cochlear lead.

6. A cochlear implant as claimed in claim 1, wherein the flexible body is formed from transparent material; and the at least one illumination guide does not extend to distal region of the cochlear lead.

7. A cochlear implant as claimed in claim 1, wherein the interface connector comprises a rigid interface connector.

8. A cochlear implant as claimed in claim 1, wherein the camera interface includes a lens that focuses light from the optical fiber bundle onto a predetermined location within the camera interface.

9. A cochlear implant for use with a micro camera including a housing, a light source and a light sensor, the cochlear implant comprising:

a stimulation assembly including a housing, an antenna within the housing, and a stimulation processor within the housing operably connected to the antenna;

a cochlear lead, operably connected to the stimulation processor, defining a proximal region and a distal region and including an electrode array with a flexible body and a plurality of electrically conductive contacts on the flexible body;

a lens associated with the distal region of the electrode array;

an optical fiber bundle, including a distal end adjacent to the lens and a proximal end, that extends from the lens, through the flexible body, and outwardly from the proximal region of the electrode array;

a camera interface, in which the proximal end of the optical fiber bundle is located, including a transparent housing with a camera receptacle that is configured to receive the micro camera in such a manner that the proximal end of the optical fiber bundle is adjacent to the light sensor; and at least one illumination guide that extends from the camera interface to the cochlear lead.

10. A cochlear implant as claimed in claim 9, wherein the transparent housing comprises a resilient transparent housing.

11. A cochlear implant as claimed in claim 9, wherein the respective configurations of the camera and the camera interface are such that the proximal end of the optical fiber bundle is no more 0.1 mm from the optical sensor when the camera is mounted to the camera interface.

12. A cochlear implant as claimed in claim 9, wherein the lens is
secured to the optical fiber bundle and projects outwardly from the flexible body,
embedded within the flexible body, or
a molded portion of the flexible body.

13. A cochlear implant as claimed in claim 9, wherein the at least one illumination guide extends to distal region of the cochlear lead.

14. A cochlear implant as claimed in claim 9, wherein the flexible body is formed from transparent material; and the at least one illumination guide does not extend to distal region of the cochlear lead.

15. A system, comprising:
a micro camera, including a housing defining an outer diameter, a light source and a light sensor; and
a cochlear implant including a stimulation assembly including a housing, an antenna within the housing, and a stimulation processor within the housing operably connected to the antenna, a cochlear lead, operably connected to the stimulation processor, defining a proximal region and a distal region and including an electrode array with a flexible body and a plurality of electrically conductive contacts on the flexible body, a lens associated with the distal region of the electrode array, an optical fiber bundle, including a distal end adjacent to the lens and a proximal end, that extends from the lens, through the flexible body, and outwardly from the proximal region of the electrode array, a camera interface, in which the proximal end of the optical fiber bundle is located, including a resilient housing with a camera receptacle defining an inner diameter that is less than the outer diameter of the camera housing and that is configured to receive the micro camera in such a manner that the proximal end of the optical fiber bundle is adjacent to the light sensor, and at least one illumination guide that extends from the camera interface to the cochlear lead.

16. A system as claimed in claim 15, wherein the respective configurations of the camera and the camera interface are such that the proximal end of the optical fiber bundle is no more 0.1 mm from the optical sensor when the camera is mounted to the camera interface.

17. A system as claimed in claim 15, wherein the lens is
secured to the optical fiber bundle and projects outwardly from the flexible body,
embedded within the flexible body, or
a molded portion of the flexible body.

18. A system as claimed in claim 15, wherein the at least one illumination guide extends to distal region of the cochlear lead.

19. A system as claimed in claim 15, wherein the flexible body is formed from transparent material; and the at least one illumination guide does not extend to distal region of the cochlear lead.

* * * * *